(12) United States Patent
Henderson et al.

(10) Patent No.: US 10,737,019 B2
(45) Date of Patent: Aug. 11, 2020

(54) INJECTION SYSTEM

(71) Applicant: Sanofi-Aventis Deutschland GmbH, Frankfurt am Main (DE)

(72) Inventors: Charley Henderson, Cambridgeshire (GB); David Cross, Letchworth (GB); Douglas Ivan Jennings, Hertfordshire (GB); Ryan Anthony McGinley, Cambridgeshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/822,807

(22) Filed: Nov. 27, 2017

(65) Prior Publication Data

US 2018/0126069 A1 May 10, 2018

Related U.S. Application Data

(62) Division of application No. 14/411,109, filed as application No. PCT/EP2013/063724 on Jun. 28, 2013, now Pat. No. 9,833,566.

(30) Foreign Application Priority Data

Jul. 6, 2012 (EP) .................................... 12175344

(51) Int. Cl.
*A61M 5/145* (2006.01)
*A61M 5/20* (2006.01)
*A61M 5/44* (2006.01)

(52) U.S. Cl.
CPC ............ *A61M 5/1452* (2013.01); *A61M 5/20* (2013.01); *A61M 5/2033* (2013.01); *A61M 5/44* (2013.01);
(Continued)

(58) Field of Classification Search
CPC ...... A61M 2205/13; A61M 2205/3576; A61M 2205/581; A61M 2205/583;
(Continued)

(56) References Cited

U.S. PATENT DOCUMENTS 6,149,626 A * 11/2000 Bachynsky ......... A61M 5/2033
604/134
2005/0197650 A1 9/2005 Sugimoto
(Continued)

FOREIGN PATENT DOCUMENTS

EP 2468338 6/2012
EP 2468340 6/2012
(Continued)

OTHER PUBLICATIONS

International Preliminary Report on Patentability in International Application No. PCT/EP2013/063724, dated Jan. 6, 2015, 5 pages.
(Continued)

*Primary Examiner* — Jason E Flick
(74) *Attorney, Agent, or Firm* — Fish & Richardson P.C.

(57) ABSTRACT

Described is a medicament cartridge comprising a housing having open proximal and distal ends, a first coupling mechanism, and a syringe slidably disposed in the housing. The syringe includes a needle and has a retracted position in which the needle is covered by the housing and an extended position in which the needle is exposed. A delivery device comprises the medicament cartridge, an actuator comprising a plunger, a motor adapted to translate the plunger, a second coupling mechanism adapted to detachably engage the first coupling mechanism, and a control button adapted to actuate the motor. A carrier comprises a first slot for at least partially containing the actuator, a second slot for at least partially
(Continued)

containing the medicament cartridge, a user interface adapted to provide at least one a visual signal and an audible signal.

19 Claims, 3 Drawing Sheets

Specification includes a Sequence Listing.

(52) U.S. Cl.
CPC ......... *A61M 5/445* (2013.01); *A61M 2205/13* (2013.01); *A61M 2205/3576* (2013.01); *A61M 2205/581* (2013.01); *A61M 2205/583* (2013.01)

(58) Field of Classification Search
CPC .... A61M 5/1452; A61M 5/20; A61M 5/2033; A61M 5/44; A61M 5/445
USPC ......................................................... 604/113
See application file for complete search history.

(56) References Cited

U.S. PATENT DOCUMENTS

| | | |
|---|---|---|
| 2008/0312604 A1 | 12/2008 | Boesen |
| 2010/0022955 A1 | 1/2010 | Slate |
| 2011/0224616 A1* | 9/2011 | Slate ........................ A61M 5/20 604/154 |
| 2013/0281936 A1 | 10/2013 | Kemp et al. |
| 2013/0291737 A1 | 11/2013 | Sims |

FOREIGN PATENT DOCUMENTS

| | | |
|---|---|---|
| EP | 2468341 | 6/2012 |
| GB | 2452286 | 3/2009 |
| JP | 2004/524117 | 8/2004 |
| JP | 2005/245852 | 9/2005 |
| JP | 2010/506674 | 3/2010 |
| JP | 2010/537683 | 12/2010 |
| JP | 2011/520569 | 7/2011 |
| JP | 2011/530361 | 12/2011 |
| WO | WO 2008/105952 | 9/2008 |
| WO | WO 2009/027621 | 3/2009 |
| WO | WO 2009/143255 | 11/2009 |

OTHER PUBLICATIONS

International Search Report and Written Opinion in International Application No. PCT/EP2013/063724, dated Nov. 6, 2013, 8 pages.

* cited by examiner

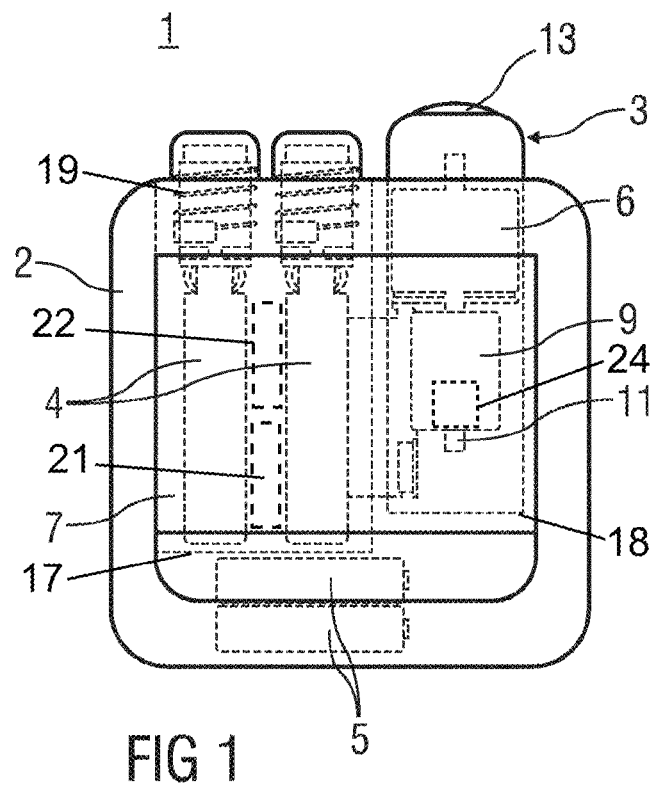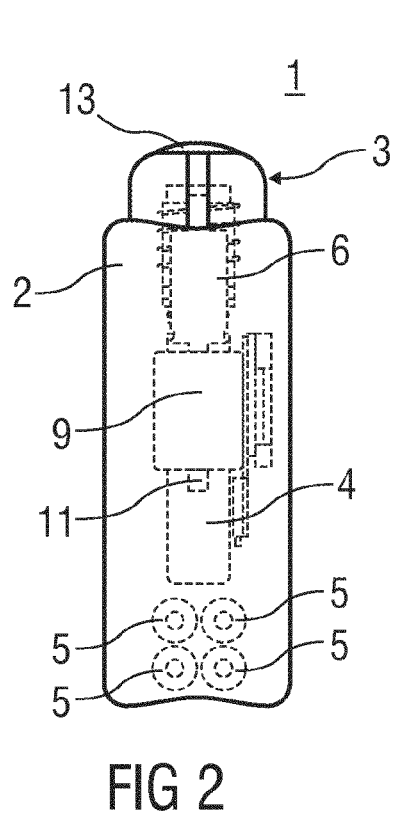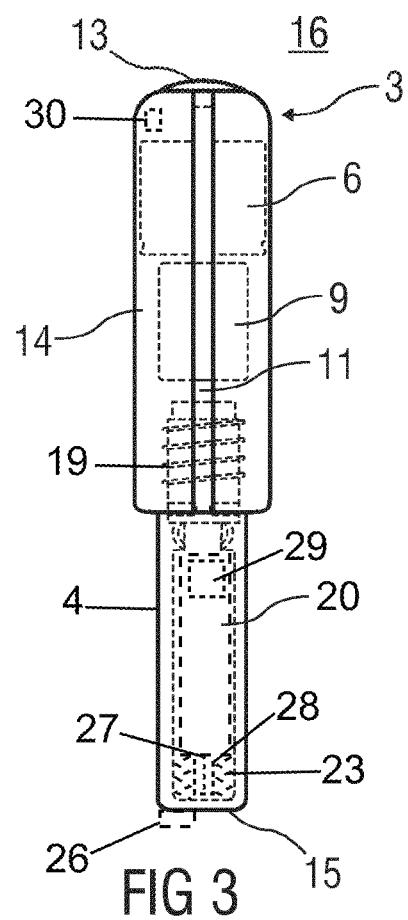

INJECTION SYSTEM

CROSS REFERENCE TO RELATED APPLICATIONS

The present application is a divisional of U.S. patent application Ser. No. 14/411,109, filed Dec. 24, 2014, which is a U.S. National Phase Application pursuant to 35 U.S.C. § 371 of International Application No. PCT/EP2013/063724, filed Jun. 28, 2013, which claims priority to European Patent Application No. 12175344.6 filed Jul. 6, 2012. The entire disclosure contents of these applications are herewith incorporated by reference into the present application.

FIELD OF INVENTION

The invention relates to an injection system for administering a medicament.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Autoinjectors may be mechanical, electro-mechanical or fully electronic. Conventional mechanical autoinjectors may automatically provide the required force for needle insertion and medicament delivery, but may not provide additional functionality (e.g., alignment verification, injection site verification, etc.) which may be capable with electro-mechanical and fully electronic autoinjectors.

Thus, there remains a need for an improved injection system.

SUMMARY

It is an object of the present invention to provide an improved injection system.

In an exemplary embodiment, a medicament cartridge according to the present invention comprises a housing having open proximal and distal ends, a first coupling mechanism, and a syringe slidably disposed in the housing. The syringe includes a needle and has a retracted position in which the needle is covered by the housing and an extended position in which the needle is exposed.

In an exemplary embodiment, the medicament cartridge further comprises a retraction spring disposed in the housing and biasing the syringe in the retracted position.

In an exemplary embodiment, the first coupling mechanism includes a thread, a snap, a latch, a hook or a bayonet coupling.

In an exemplary embodiment, the medicament cartridge further comprises a contact sensor disposed on a contact surface of the housing. The contact sensor is adapted to generate a signal when the contact surface is placed on an injection site.

In an exemplary embodiment, a delivery device according to the present invention comprises a medicament cartridge as described herein, an actuator comprising a plunger, a motor adapted to translate the plunger, a second coupling mechanism adapted to detachably engage the first coupling mechanism, and a control button adapted to actuate the motor.

In an exemplary embodiment, translation of the plunger in a first axial direction pushes the syringe from the retracted position to the extended position. When the syringe is in the extended position, translation of the plunger in the first axial direction pushes a stopper in the syringe.

In an exemplary embodiment, the actuator further comprises an energy source.

In an exemplary embodiment, a carrier according to the present invention comprises a first slot for at least partially containing an actuator as described herein, a second slot for at least partially containing a medicament cartridge as described herein, and a user interface adapted to provide at least one a visual signal and an audible signal.

In an exemplary embodiment, the carrier further comprises a first energy source including a disposable battery, a rechargeable battery or a connector adapted to couple to an external power source.

In an exemplary embodiment, the user interface includes at least one of a display screen, a light emitting diode, a speaker, a microphone, a button and a dial.

In an exemplary embodiment, the carrier further comprises a drug tempering unit adapted to heat or cool the cartridge.

In an exemplary embodiment, the carrier further comprises a temperature sensor adapted to sense a temperature of the cartridge.

In an exemplary embodiment, the carrier further comprises a first communication device adapted to communicate with a second communicate device in the actuator.

In an exemplary embodiment, the visual signal includes at least one of alphanumeric or graphical data on the display screen and a change in color or illumination sequence of the light emitting diode, and the audible signal includes at least one a tone, an instruction, and a message regarding progress of an injection.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 is a schematic front view of an exemplary embodiment of an injection system according to the present invention, FIG. 2 is a schematic lateral view an exemplary embodiment of an injection system according to the present invention, FIG. 3 is a schematic front view of an exemplary embodiment of a delivery device according to the present invention.

Corresponding parts are marked with the same reference symbols in all figures.

DETAILED DESCRIPTION

Figure 4:
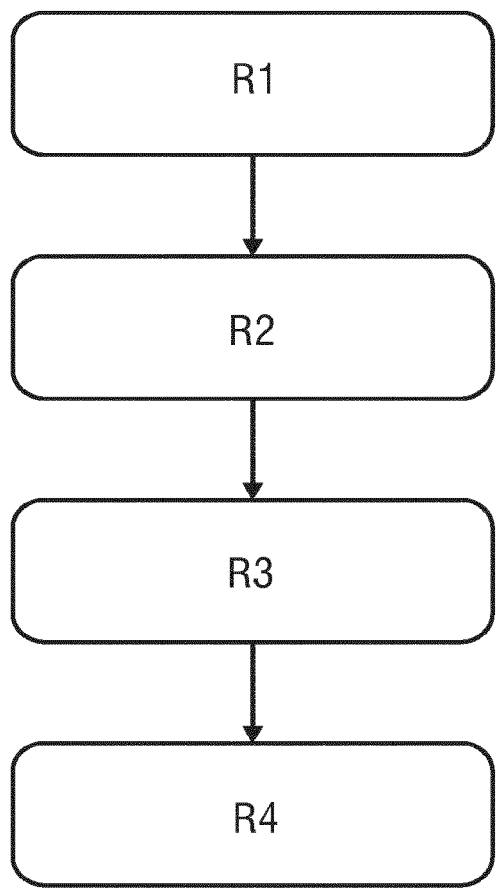
FIG. 4 is an exemplary embodiment of a method for initializing an injection system according to the present invention.

FIG. 1 is a schematic front view of an exemplary embodiment of an injection system 1 and FIG. 2 is a schematic lateral view of an exemplary embodiment of an injection system 1 according to the present invention.

In an exemplary embodiment, the injection system 1 comprises a carrier 2 adapted to hold an actuator 3 and at least one cartridge 4. For example, the carrier 2 may include a first slot 17 to releasably hold the actuator 3 and a second slot 18 to releasably hold the at least one cartridge 4. In an exemplary embodiment, the cartridge 4 includes a housing adapted to hold a syringe 20 containing a medicament. The housing may include a first coupling mechanism 19 (e.g., threads, snaps, latches, hooks, etc.) adapted to detachably engage a second coupling mechanism 24 on the actuator 3. The syringe 20 may be axially translatable relative to the housing between a retracted position and an extended position. A retraction spring 23 disposed in the housing may bias the syringe 20 in the retracted position. The syringe 20 includes a translatable stopper adapted to expel the medicament via a needle on the syringe 20. The needle may be covered by a removable needle boot.

In an exemplary embodiment, the cartridge 4 includes a contact surface 15 adapted to contact an injection site. A contact sensor may be coupled to the contact surface 15 to detect physical contact with the injection site.

In an exemplary embodiment, the carrier 2 includes a first energy source 5 (e.g., disposable or rechargeable batteries, a connector for connecting to an external power source), a data processing unit (not illustrated) and a communication device adapted for wired (e.g., USB, Ethernet, etc.) and/or wireless communications (e.g., cellular, 802.1x, etc.). The carrier 2 may also include a user interface (e.g., display screen 7, LEDs, speaker, microphone, buttons, dials, etc.) adapted to notify the user of conditions, events or actions to be performed, and/or allow the user to input respond to information requests (e.g., for compliance with a treatment schedule).

In an exemplary embodiment, the carrier 2 includes a drug tempering unit 22 (e.g., a Peltier element) adapted to heat and/or cool the cartridge 4. The drug tempering unit 22 may further include a temperature sensor 21 which transmits a signal to the data processing unit for heating and/or cooling the cartridge 4, as necessary.

In an exemplary embodiment, the actuator 3 includes a case 14 having the second coupling mechanism 24 adapted to detachably engage the first coupling mechanism 19 on the housing of the cartridge 4. A motor 9 disposed in the case 14 may be adapted to displace a plunger 11 for applying an axial force on the syringe 20 in the cartridge 4, e.g., for needle penetration, and for applying an axial force on the stopper in the syringe 20, e.g., for delivering the medicament.

In an exemplary embodiment, an encoder (not illustrated) may be utilized by the actuator 3 to detect the position of the plunger 11.

In an exemplary embodiment, the actuator 3 includes a control button 13 which actuates the motor 9. In an exemplary embodiment, the control button 13 may be inoperable until the cartridge 4 has been coupled to the actuator 3.

In an exemplary embodiment, the actuator 3 includes a second energy source 6 (e.g., a supercapacitor chargeable by the first energy source 5 when the actuator 3 is coupled to the carrier 2), a second data processing unit (not illustrated) and a second communication device adapted for wired and/or wireless communications with the first communication device in the carrier 2.

In an exemplary embodiment, the first and second communication device may include radios which utilize a short range wireless communication protocol, e.g., Bluetooth or Zigbee, or other short range communication devices, e.g., infrared.

FIG. 3 shows an exemplary embodiment of a delivery device 16 in which the actuator 3 is coupled to the cartridge 4.

FIG. 4 shows an exemplary embodiment of a method for initializing an injection system according to the present invention.

In step R1, the carrier 2 is turned on. For example, the carrier 2 may include a power switch. When the carrier 2 is turned on, the user interface may provide information and/or prompts. For example, the display screen 7 may indicate temperature of the cartridge(s) 4, power level of the actuator 3, an injection schedule, etc. The carrier 2 may include one or more locks to prevent removal of the actuator 3 and/or the cartridges 4. When the carrier 2 is turned on, the lock(s) may be released.

In step R2, the actuator 3 is removed from the carrier 2.

In step R3, the actuator 3 is coupled to a cartridge 4. In an exemplary embodiment, a proximal end of the cartridge 4 may include a removable cover or be covered by a slidable door on the carrier 2. In an exemplary embodiment, the carrier 2 may provide an indication (e.g., LED illumination, message on display screen 7, etc.) which indicates the cartridge 4 that should be selected. When the actuator 3 is coupled to the cartridge 4, the first coupling mechanism 19 20 engages the second coupling mechanism 24. A feedback (e.g., an audible click, a color change of a light emitting element 30 on the actuator 3, etc.) may be provided to notify the user that an injection may be administered.

In step R4, the cartridge 4, coupled to the actuator 3, is removed from the carrier 2. A grip in the carrier 2 may engage the needle boot on the needle of the syringe 20 so that when the cartridge 4 is removed, the needle boot remains in the carrier 2. However, the needle may be contained (and not visible) within the housing of the cartridge 4 in a retracted position.

Figure 5:
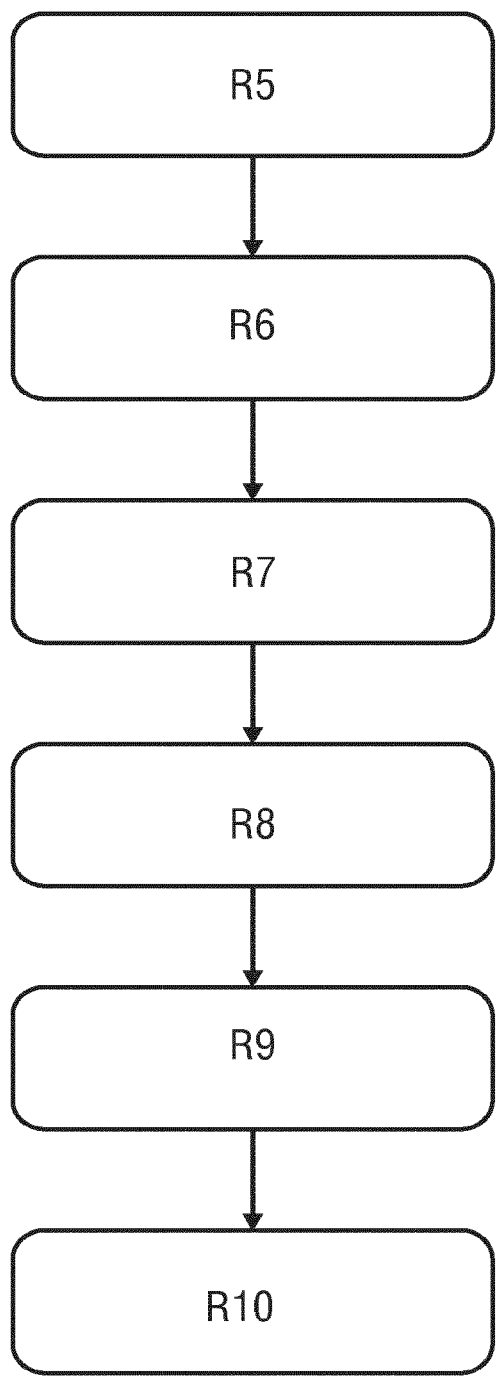
FIG. 5 is an exemplary embodiment of a method for performing an injection with an injection system according to the present invention.

FIG. 5 is an exemplary embodiment of a method for performing an injection with an injection system according to the present invention.

In step R5, the cartridge 4, coupled to the actuator 3, is placed on an injection site. In an exemplary embodiment, the contact sensor on the cartridge 4 may communicate a signal to the data processing unit in the actuator 3 which may provide a feedback to the user (e.g., a change in color the light emitting element on the actuator 3, a message on the display screen 7 of the carrier, an audible alert), notifying the user that the injection may be administered.

In step R6, the control button 13 is pressed and the motor 9 is activated.

In step R7, the motor 9 displaces the plunger 11 to advance the syringe 20 relative to the housing of the cartridge 4 from the retracted position to the extended position for insertion of the needle into the injection site. Axial movement of the syringe 20 may compress the retraction spring 23.

In step R8, the motor 9 displaces the plunger 11 to advance the stopper relative to the syringe 20 for delivery of the medicament.

In step R9, the motor 9 is disabled, because the data processing unit has received a signal from the encoder which indicates that the plunger 11 has traveled a distance corresponding to the delivery of a full dose of the medicament. When the motor 9 is disabled, the force in the retraction spring 23 may push the syringe 20 back to the retracted position in the housing of the cartridge 4. In an exemplary embodiment, when the motor 9 is disabled, it may disengage the plunger via, for example, a clutch or ratchet arrangement.

In step R10, the cartridge 4 may be returned to the carrier 2. When the cartridge 4 is inserted into the carrier 2, the needle boot may re-cover the needle of the syringe 20. In an exemplary embodiment, the actuator 3 and/or the carrier 2 may include a release mechanism which disengages the first and second coupling mechanisms 19, 24. For example, the release mechanism may be a button on the actuator 3 which is pressed to release the cartridge 4. In another example, the release mechanism may include an arm which deflects a resilient latch on the actuator 3 that is holding the cartridge 4.

In another exemplary embodiment, the cartridge 4 may be disengaged from the actuator 3 and deposited in a sharps bin or other receptacle.

In any one or more of the above-described steps, the carrier 2 may provide feedback regarding the injection process. For example, when the carrier 2 is turned on, the display screen 7 may indicate temperature of the cartridge(s) 4, power level of the actuator 3, an injection schedule, etc. For example, during the injection, the carrier 2 may provide feedback regarding injection time remaining, reassuring messages about the benefits of the medicament, etc. For example, after the injection, the carrier 2 may provide visual and/or audible reminders about a next scheduled injection, benefits of compliance with a treatment schedule, etc.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A delivery device comprising:
a medicament cartridge comprising:
a housing having open proximal and distal ends,
a first coupling mechanism, and
a syringe slidably disposed in the housing, the syringe including a needle and a stopper; and
an actuator detachably engageable with the housing of the medicament cartridge via the first coupling mechanism, the actuator comprising a plunger translatable distally in a first axial direction to push the syringe from a retracted position in which the needle is covered by the housing to an extended position in which the needle is exposed, and to push the stopper distally relative to the housing.

2. The delivery device according to claim 1, further comprising a retraction spring disposed in the housing of the medicament cartridge and biasing the syringe into the retracted position.

3. The delivery device according to claim 2, wherein the retraction spring is configured to be compressed when the syringe is pushed from the retracted position to the extended position.

4. The delivery device according to claim 2, wherein the retraction spring is configured to move the syringe from the extended position into the retracted position when a force on the syringe is removed.

5. The delivery device according to claim 1, wherein the first coupling mechanism includes a thread, a snap, a latch, a hook, or a bayonet coupling.

6. The delivery device according to claim 1, further comprising a contact sensor disposed on a contact surface of the housing, the contact sensor adapted to generate a signal when the contact surface is placed on an injection site.

7. The delivery device according to claim 6, wherein the contact sensor is configured to communicate the signal to a processing unit to provide user feedback.

8. The delivery device according to claim 1, wherein the syringe contains a medicament, and the stopper is configured to be pushed into the syringe to deliver the medicament from the syringe.

9. The delivery device according to claim 1, wherein the actuator comprises a motor operable to
translate the syringe relative to the housing for needle insertion, and

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35 apply a force on the stopper of the syringe for medicament delivery.

10. The delivery device according to claim 1, wherein the first coupling mechanism is configured to detachably engage the housing to the actuator to enable operation of a control button of the actuator.

11. The delivery device according to claim 1, wherein the first coupling mechanism is configured to cause user feedback to be provided when the first coupling mechanism is detachably engaged to an actuator comprising the plunger.

12. The delivery device according to claim 1, further comprising a needle boot covering the needle of the syringe,
wherein the needle boot is configured to be removed from the needle of the syringe when the medicament cartridge is removed from a carrier containing the medicament cartridge.

13. The delivery device according to claim 12, wherein the needle boot is configured to cover the needle of the syringe when the medicament cartridge is placed into the carrier.

14. The delivery device according to claim 1, wherein the first coupling mechanism is insertable into a case of the actuator.

15. The delivery device according to claim 14, wherein the housing is configured to receive the plunger of the actuator when the first coupling mechanism is engaged to the actuator.

16. The delivery device according to claim 1, wherein the first coupling mechanism is disposed on the proximal end of the housing, and a contact surface is disposed on the distal end of the housing.

17. The delivery device according to claim 1, wherein the needle is configured to be exposed for needle insertion when the syringe is pushed into the extended position.

18. A delivery device comprising:
a medicament cartridge comprising:
a housing having open proximal and distal ends,
a first coupling mechanism, and
a syringe slidably disposed in the housing, the syringe including a needle;
an actuator detachably engageable with the housing of the medicament cartridge via the first coupling mechanism, the actuator comprising:
a plunger translatable distally relative to the housing of the medicament cartridge to push the syringe from a retracted position in which the needle is covered by the housing to an extended position in which the needle is exposed when a plunger is translated in a first axial direction, and
a control button configured to be inoperable to actuate the actuator until the actuator is engaged to the housing of the medicament cartridge via the first coupling mechanism.

19. A medicament cartridge comprising:
a housing having open proximal and distal ends;
a first coupling mechanism; and
a syringe slidably disposed in the housing, the syringe including a needle, the syringe being configured to be pushed from a retracted position in which the needle is covered by the housing to an extended position in which the needle is exposed when a plunger is translated in a first axial direction,
wherein the first coupling mechanism is configured to cause a light emitting element to provide user feedback when the first coupling mechanism is detachably engaged to an actuator comprising the plunger.

* * * * *